United States Patent
Flohr et al.

(10) Patent No.: US 6,252,926 B1
(45) Date of Patent: Jun. 26, 2001

(54) METHOD FOR THE RECONSTRUCTION OF IMAGES FROM MEASURED VALUES ACQUIRED WITH A CT APPARATUS BY SPIRAL SCAN AND CT APPARATUS FOR THE IMPLEMENTATION OF THE METHOD

(75) Inventors: Thomas Flohr, Uehlfeld; Stefan Schaller, Fuerth, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/351,466

(22) Filed: Jul. 12, 1999

(30) Foreign Application Priority Data

Jul. 17, 1998 (DE) .............................................. 198 32 276

(51) Int. Cl.$^7$ ...................................................... A61B 6/03
(52) U.S. Cl. ............................................... 378/15; 378/901
(58) Field of Search .................................. 378/4, 15, 901

(56) References Cited

U.S. PATENT DOCUMENTS

| | | |
|---|---|---|
| 4,994,965 | 2/1991 | Crawford et al. . |
| 5,251,128 | 10/1993 | Crawford . |
| 5,262,946 * | 11/1993 | Heuscher .............................. 378/15 |
| 5,396,418 * | 3/1995 | Heuscher .............................. 378/15 |
| 5,875,225 | 2/1999 | Wallschlaeger ........................ 378/15 |
| 5,987,157 | 11/1999 | Schaller et al. ...................... 382/131 |

FOREIGN PATENT DOCUMENTS

| | | |
|---|---|---|
| 196 14 223 | 4/1987 | (DE) . |
| 0 713 677 | 5/1996 | (EP) . |

OTHER PUBLICATIONS

"Dual–Slice Spiral Versus Single–Slice Spiral Scanning: Comparison Of The Physical Performance Of Two Computed Tomography Scanners," Liang et al, Med. Phys, vol. 23, No. 2, Feb. 1996, pp. 205–220.

* cited by examiner

Primary Examiner—David V. Bruce
(74) Attorney, Agent, or Firm—Schiff Hardin & Waite

(57) ABSTRACT

In a method and computed tomography (CT) apparatus for the reconstruction of images from CT measured values acquired by spiral scan that are respectively allocated to one of a number of projection angles and a z-position on the longitudinal axis of the spiral scan, for each projection angle, all measured values belonging thereto and to the corresponding complementary projection angle and lying within a maximum spatial distance from the image plane, and lying within a maximum time from a reference time, are employed in the reconstruction, respectively weighted according to their spatial and time position.

12 Claims, 9 Drawing Sheets

METHOD FOR THE RECONSTRUCTION OF IMAGES FROM MEASURED VALUES ACQUIRED WITH A CT APPARATUS BY SPIRAL SCAN AND CT APPARATUS FOR THE IMPLEMENTATION OF THE METHOD

BACKGROUND OF THE INVENTION

1. Field of the Invention

The present invention is directed to a method for the reconstruction of images with respect to an image plane from measured values acquired with a CT apparatus provided with a detector having at least one line, but preferably a number of lines, of detector elements by conducting a spiral scan, the measured values being respectively allocated to one of a number of projection angles α and to a z-position on the longitudinal axis of the spiral scan. The invention is also directed to a CT apparatus for the implementation of such a method.

2. Description of the Prior Art

In the reconstruction of images from measured values acquired by spiral scanning with CT apparatus having a single-line detector, an interpolation between the measured values lying in front of and behind the image plane is implemented for each projection angle for generating calculated projections in the desired image plane.

Two interpolation methods are currently most standard:

In the first, a linear interpolation is undertaken between respectively two measured projections lying closest to the image plane, these having been registered at the same projection angle α but in different revolutions. This type of interpolation is known as 360LI interpolation. In the second method, interpolation is carried out between respectively two projections lying closest to the image plane, of which one projection was registered at the projection angle ad and the other was registered at the projection angle $\alpha_c$ complementary thereto. $\alpha_c = \alpha_d \pm \pi$ is valid for the middle detector element of the detector. This type of interpolation is known as 180LI interpolation. Given the same pitch, it supplies narrower effective layer widths (characterized, for example, by the full width at half maximum FWHM of the layer sensitivity profile) than the 360LI interpolation. Given the same output power of the x-ray tube (mA value), the pixel noise is increased in comparison to the 360LI interpolation as a trade off. The artifact susceptibility is also higher. Both interpolation types are illustrated schematically in FIG. 2 for the pitch p=2, FIG. 2 showing the projection angle α as a function of the detector position in the z-direction, with the projection angle α entered on the longitudinal axis of the spiral scan (z-position) over the position normalized to the width b of a line of the detector. The pitch p is defined as the ratio of the shift in the z-direction per revolution (between the x-ray source/detector and the subject) in mm and the width (in the z-direction) of a line of the detector in mm.

Reconstruction of images from measured values acquired by spiral scan with exact and approximative methods is known for a CT apparatus with multi-line detectors (for example, German PS 196 14 223). These known methods take the exact geometry into consideration but are in part extremely calculation-intensive and therefore poorly suited for use in a commercial CT apparatus.

For reducing the calculating outlay given a low number M of lines (for example, M≦5) of the detector, the angle of inclination of the scan rays relative to a plane proceeding perpendicularly to the longitudinal axis of the spiral scan (referred to as the z-axis), known as the cone angle, can be left out of consideration, and the standard 360LI and 180LI interpolation for an apparatus with a single-line detector can be transferred to a number of detector lines. This is the reconstruction technique in the commercial CT apparatus "Elscint Twin" that has a two-line detector (see "Dual-slice versus single-slice spiral scanning: Comparison of the physical performances of two computed tomography scanners", Yun Liang and Robert A. Kruger, Med. Phys. 23(2), February 1996, pp. 205–220). The principle of the 180LI and 360LI interpolation transferred to a number of lines is illustrated in FIG. 3 with reference to the arbitrarily selected example of a 4-line scanner at pitch 3.

The weightings to be taken into consideration in the interpolation are calculated "on the fly" for the interpolation function that has been selected (for example, a triangular function for linear interpolation), this being defined in the apparatus and being capable of being changed only with great difficulty. Given a detector with several lines, the method rapidly encounters practical limits because of the completely modified, relative position of the scan rays on the z-axis for each pitch p.

In the conventional 180LI and 360LI interpolation for a multi-line detector, the slice sensitivity profile for every pitch value p and the pixel noise arising at a fixed output power of the X-ray tube are permanently predetermined by the position of the scan rays on the z-axis. The pixel noise exhibits an unexpected and very sensitive dependency on the pitch p. For example, the scan rays of all four detector lines for a 4-line detector given the pitch p=1 are incident on the same z-positions in successive revolutions. Therefore they can simply be averaged before the interpolation, and a dose accumulation by the factor 4, and thus a halving of the pixel noise by comparison to the one-liner with 360LI interpolation, occurs as a result. When the pitch p is increased only slightly, for example to p=1.1, this multiple scanning is eliminated. A narrower slice sensitivity profile is obtained in the 180LI and 360LI interpolation, but at the expense of the same pixel noise as for a one-line detector. According to the known method, it is not possible, given small pitch values (for example, p=1.1, as above), to utilize the overlapping scanning in the z-direction for the purpose of reducing the pixel noise while simultaneously broadening the slice sensitivity profile.

Given the known methods provided for employment with multi-line detector, moreover, the measured values of all lines of the detector are weighted for each projection angle only according to their distance from the image plane, without considering the time at which the measured values were acquired. As a result, an enlargement of the time window during which measured values are acquired that contribute to an image derives as the pitch becomes smaller. For a 4-line detector and a pitch p=1, for example, not only is the aforementioned quadrupling of the dose in the image obtained compared to a one-line CT apparatus, but also a lengthening of the image-relevant window occurs to four times the duration of a complete revolution of the X-ray source. Particularly in exposures of moving subjects such as, for example, high-resolution lung exposures, this can lead to a noticeable limitation of the image quality.

SUMMARY OF THE INVENTION

An object of the present invention is to provide a CT image reconstruction method of the type initially described wherein the prerequisite is established for being able to arbitrarily set the slice sensitivity profile. It is also an object of the invention to provide a CT apparatus for the implementation of such a method.

The above object is achieved in accordance with the principles of the present invention in a method and a computed tomography apparatus wherein an image of a slice of an examination subject is reconstructed from measured values, the slice having a slice thickness with respect to an image plane, employing a spiral scan wherein an x-ray source and a radiation detector rotate around an examination subject with a relative longitudinal shift of the x-ray source and the detector occurring with respect to the examination subject during each revolution, the measured values from the radiation detector being respectively allocated to one of a number of projection angles α and to a z-position on the longitudinal axis of the spiral scan, while adhering to a constant, dimensionless pitch p during the spiral scan, the pitch being the ratio of the relative longitudinal shift and a width in the longitudinal direction of a line of the radiation detector, and wherein a reference time associated with the spiral scan is defined, and for each projection angle, a set of measured values is allocated thereto which lie within a maximum distance from the image plane and which were obtained within a maximum time from the reference time, and wherein the measured values are weighted using a first weighting function dependent on the respective spatial distances of the measured values along the longitudinal axis, and using a second weighting function dependent on the respective times of the values relative to the reference time. The image of the slice of the examination subject is reconstructed from this set of weighted measured values.

The inventive method employs a new type of weighting for measured values acquired by spiral scanning with a CT apparatus having single-line detector or a multi-line detector, wherein, in addition to the spatial distance of a measured projection and of the corresponding measured values, from the image plane, the time spacing of the projection from a reference time, i.e. from a reference projection (for example, that was registered with focus position lying in the image plane) is also taken into consideration. A two-dimensional location and time weighting thus is undertaken. By a suitable selection of the weighting function, a desired slice sensitivity profile as well as a desired time sensitivity profile therefore can be set in the z-direction. Dependent on the selection of the weighting function, in particular, the user can set the ratio of dose utilization and time resolution for a given spatial slice sensitivity profile, and the ratio of dose utilization and the z-resolution for a given time slice sensitivity profile, nearly arbitrarily for the same spiral scan.

In the inventive CT apparatus, thus, the two-dimensional location and time weighting can ensue with a practically arbitrarily selectable weighting function. This enables the realization of nearly arbitrary slice sensitivity profiles in the z-direction as well as nearly arbitrary time-sensitivity profiles.

In the inventive CT apparatus, the weighting functions can be selected and exchanged similar to CT convolution kernels since they are efficiently entered and stored in pre-calculated tables.

DESCRIPTION OF THE PREFERRED EMBODIMENTS

Figure 1:
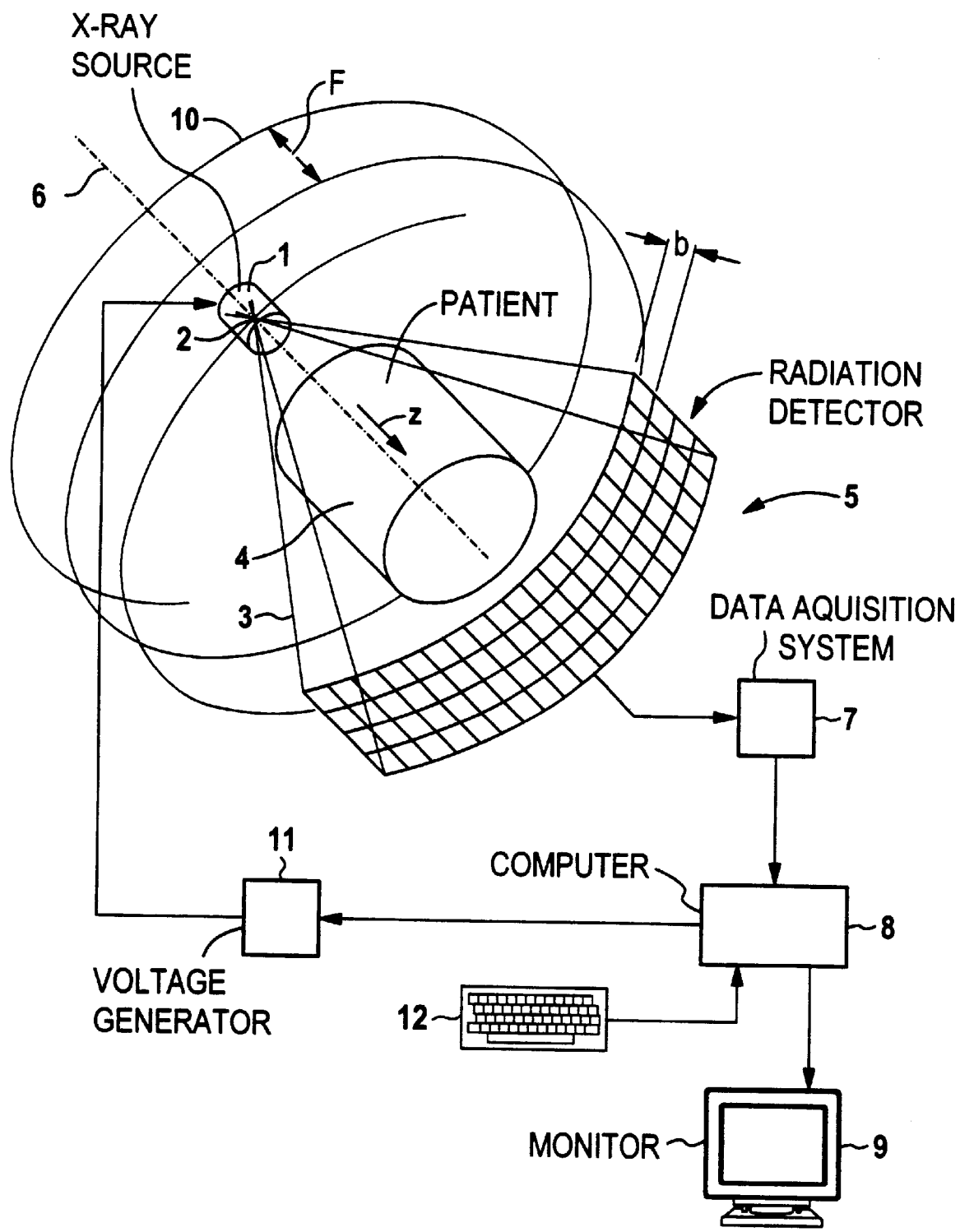
FIG. 1 is a schematic illustration of an inventive CT apparatus for the implementation of the inventive method.
Figure 2:
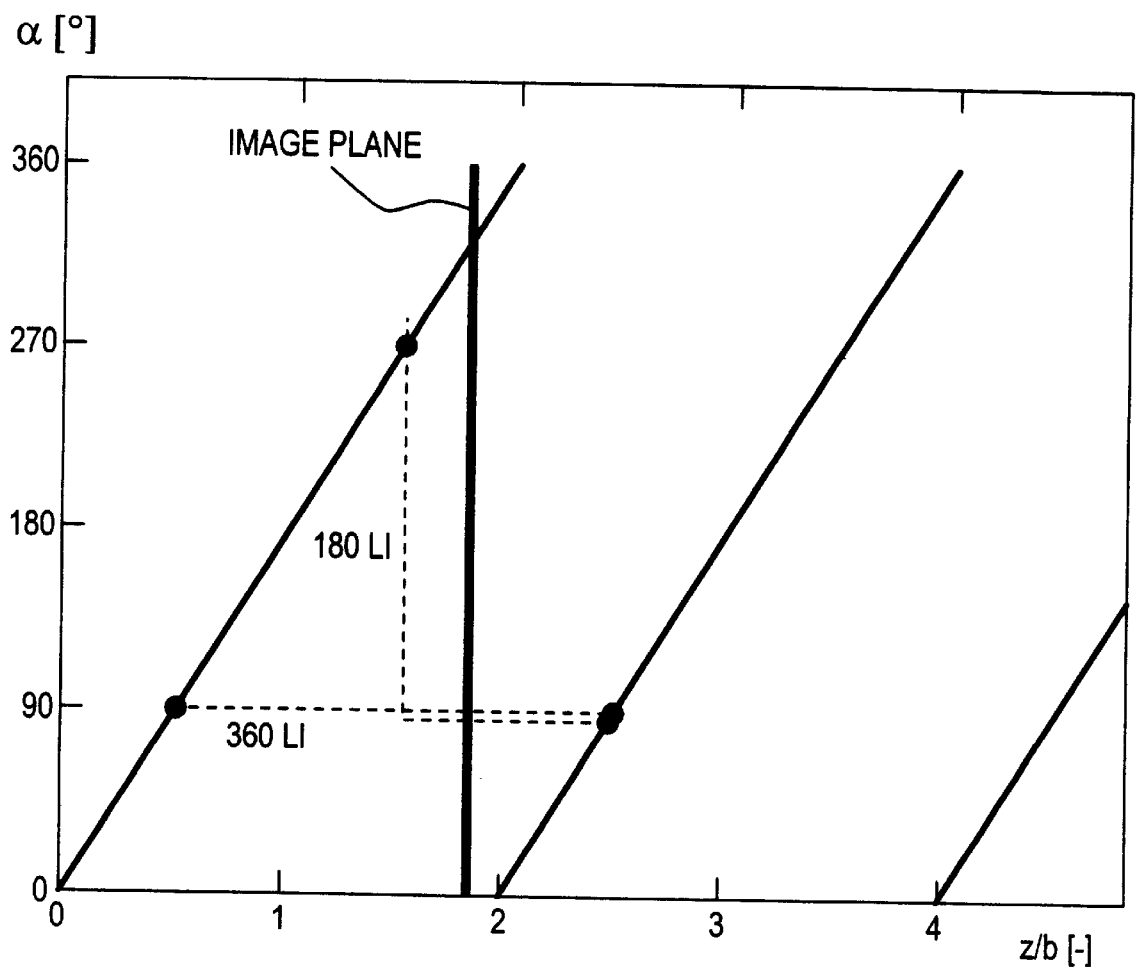
FIG. 2, as noted above, is a diagram illustrating the known interpolation methods which are standard in conventional reconstruction methods for CT apparatus having a single-line detector.
Figure 3:
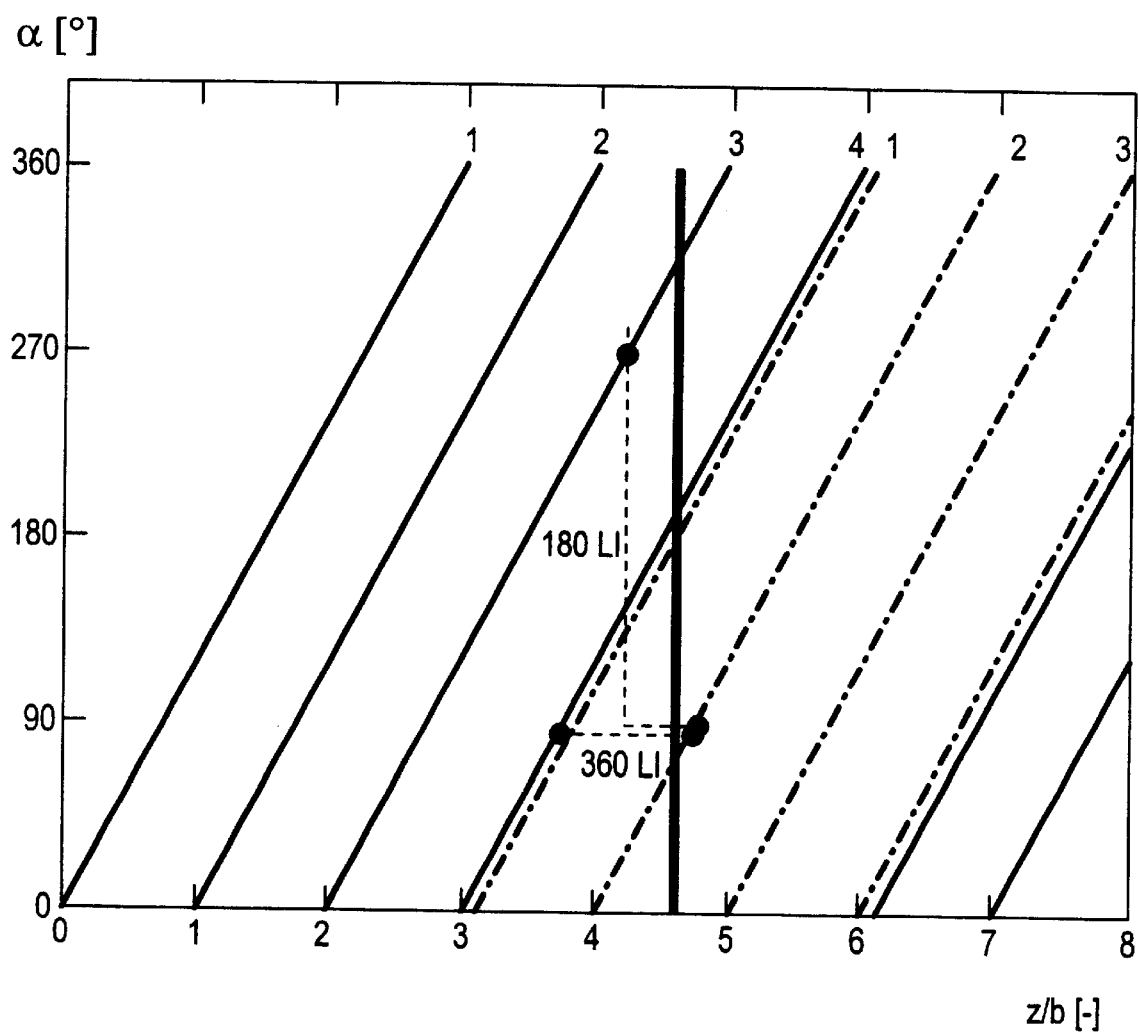
FIG. 3, as noted above, illustrate, analogous to FIG. 2, the corresponding diagram for a CT apparatus with 4-line detector.

In a schematic fashion, FIG. 1 shows a CT apparatus provided for the implementation of the inventive method that has an x-ray source 1, for example an x-ray tube with a focus 2, from which a pyramidal x-ray beam 3 gated by a diaphragm (not shown) emanates, which penetrates an examination subject 4, for example a patient, and is incident on a detector 5. The detector 5 is composed of a number of parallel detector lines each formed by a row of detector elements. The x-ray source 1 and the detector 5 form a measuring system that is rotatable around a system axis 6, so that the examination subject 4 is trans-irradiated from different projection angles α. Using the output signals of the detector elements of the detector 5 that thereby occur, a data acquisition system 7 forms measured values—referred to below as measured projections—that are supplied to a computer 8 that calculates an image of the examination subject 4 that is reproduced on a monitor 9.

A scanning of larger volumes of the examination subject 4 is possible by causing the measuring system 1, 5 to undertake a spiral scan of the desired volume, as illustrated in FIG. 1 by a spiral (helix) 10. A relative movement between the measuring arrangement composed of x-ray source 1 and the detector 5 and the examination subject 4 thereby ensues in the direction of the system axis 6, which thus simultaneously represents the longitudinal axis of the spiral scan.

A keyboard 12 that enables the operation of the CT apparatus is connected to the computer 8, this simultaneously assuming the control of the CT apparatus in the described exemplary embodiment (it is also possible to provide a separate computer for this purpose).

In particular, it is possible to set the pitch p of the spiral scan via the keyboard 12. The pitch p is the quotient of the aforementioned shift in the z-direction occurring during a revolution of the measuring system and the width b of a line of the detector in z-direction in mm. The computer 8 also serves the purpose of setting the tube current of the x-ray source 1, supplied by a voltage generator 11.

The transirradiation from different projection angles is undertaken for the purpose of acquiring measured projections. To that end, the x-ray source I transirradiates the examination subject 4 with the x-ray beam 3 emanating from successive positions of the focus 2 lying on the spiral 10, whereby each position of the focus 2 is allocated to a projection angle and to a z-position with respect to the system axis 6.

As a result of the spiral scan, at most one measured projection can exist with respect to an image plane proceeding at a right angle relative to the system axis 6, this projection having been registered with a position of the focus 2 lying in this image plane. In order nonetheless to be able to calculate an image of the slice of the examination subject 4 belonging to the respective image plane, measured projections registered in the proximity of the image plane must be acquired by suitable interpolation methods in calculated projections lying in the image plane, with each calculated projection, as in the case of measured projections, being allocated to a projection angle α and to a z-position with respect to the system axis 6.

The inventive method is explained below with reference to the example of a CT apparatus having a 4-line detector, but this does not represent a limitation of the underlying principle. The applicability to other line numbers M≠4 will be clear to those skilled in the art.

The calculation of an image for the position $z_{ima}$ of the image plane on the longitudinal axis of the spiral scan is described in detail below. The index ima stands for image.

As first processing step, the computer 8 generates a parallel projection (with respect to the projection angle) from the measured fan projections by a standard rebinning in the azimuthal direction. This is known as azimuthal re-binning and is separately implemented for all M lines, as for measured values acquired with a single-line detector. The computer 8 thus only considers the data of a line without taking its respective z-position into consideration. The measured data f (l, k, i, v) thereby arise. I=1, 2 ... $N_{P,\pi}$ is the (parallel) projection number, whereby $N_{P,\pi}$ is the number of projections registered during half a revolution of the x-ray source 1, k is the detector channel, i=1, 2, 3, 4 is the number of the detector line and v is the number of the half revolution of the x-ray source 1 from which the appertaining projection derives. By specifying the number of the half revolution v, whether this is a direct or a complementary projection is also defined at the same time. All projections having even numbers of the half revolution v can, for example, be direct projections for a specific image plane; all projections with odd numbers of the half revolution v are then complementary projections. For another image plane, projections having even and odd numbers of the half revolution v can change roles. This is an important advantage since, differing from conventional methods on the basis of fan projection, "complementary" and "direct" projections are identical with respect to their properties. The allocation "direct" and "complementary" derives only from the z-position of the respective image plane. The interpolation between direct and between direct and complementary projections therefore can be described in a uniform framework.

The magnitudes of all measured values f (l, k, i, v) within a certain, selectable maximum distance $|z_{max}|$ from the image plane are taken into consideration by the computer 8 for each projection angle $\alpha_l$, differing from the conventional 180LI and 360LI interpolation. v is the number of the half revolution from which the appertaining projection derives. The respective number of the half revolution v thus defines the point in time at which the projection identified by the projection number l and the number i of the line of the detector was obtained, which is important when data from a number of spiral revolutions contribute to the image.

All available measured values within $[z_{ima}-z_{max}, z_{ima}+z_{max}]$ for each l are weighted according to a first weighting function according to their distance $\Delta z_{lkiv}$ from the image plane. In addition to the weighting in z-direction, moreover, a time weighting occurs according to a second weighting function, namely according to the time spacing of the projection from a reference time at which a reference projection was registered, for example the projection at which the focus lies in the image plane. Let $v_{ref}$ be the number of the half revolution from which the reference projection derives and $t_{ref}$ be the time at which it was registered. For each projection identified by l,i and v, the computer 8 then calculates its time distance $\Delta t_{lkiv}$ from $t_{ref}$ and $$p(l,k) = \frac{\sum_i \sum_v g(\Delta z_{lkiv}) w(\Delta t_{lkiv}) f(l,k,i,v)}{\sum_i \sum_v g(\Delta z_{lkiv}) w(\Delta t_{lkiv})} \quad (1)$$

is obtained as resulting, calculated overall projection P(l,k). The function g ( ) is the first, spatial weighting function in the z-direction. The function w( ) is the second, time function that can be arbitrarily selected (within certain limits). The division by the sum of all weightings ensues because, due to the inventive type of weighting, a different number of measured values may have to be considered for each projection angle, but the total weighting of all measured values taken into consideration must always be 1. When, as in the above equation, the normalizing is implemented in common for all v, the computer 8 treats all "direct" and "complementary" projections the same, as a generalization of a 180LI interpolation. Given a 360LI interpolation, the sum of all weightings is simply separately formed for even v and for odd v, and the contributions for even v and odd v are separately normalized. By contrast to the CT apparatus with a one-line detector, the time weighting given a multi-line CT apparatus and small pitch values is possible because interpolation can be optionally carried out between data of the various detector lines measured at the same point in time and between measured values from different half revolutions.

For the special case of w( )=constant covered by the invention, the computer 8 foregoes a time weighting, i.e. the computer 8 treats all measured values the same regardless of their measuring time. By selecting $|z_{max}|$ and the weighting function g( ),however, the computer 8 still always can set any desired spatial slice sensitivity profile. This procedure also can be employed for the reconstruction of images on the basis of measured data that were acquired by spiral scanning using a single-line detector.

In the general case, the normalizing of the weightings enables arbitrary scan patterns of the scan rays on the z-axis, i.e. all scan patterns that are pitch-dependent given multi-line detectors.

The weightings $g(\Delta z_{lkiv})$ and $w(\Delta t_{lkiv})$ are stored in tables in a suitable memory of the computer 8, these tables having been pre-calculated pitch-dependent. Due to the utilization of symmetries, the tables need only a small amount of memory space and can be efficiently addressed. At the beginning of each reconstruction, the corresponding weighting table is calculated from the weighting functions g( ) and w( ). In this context, a modification of the interpolation functions merely means a recalculation of the weighting tables with modified g( ) and/or w( ). The selection of the weighting functions and the z-resolution and time resolution thereby characterized thus can be fundamentally designed like the selection of CT convolution kernels; in particular, new weighting functions can be easily introduced.

Figure 4:
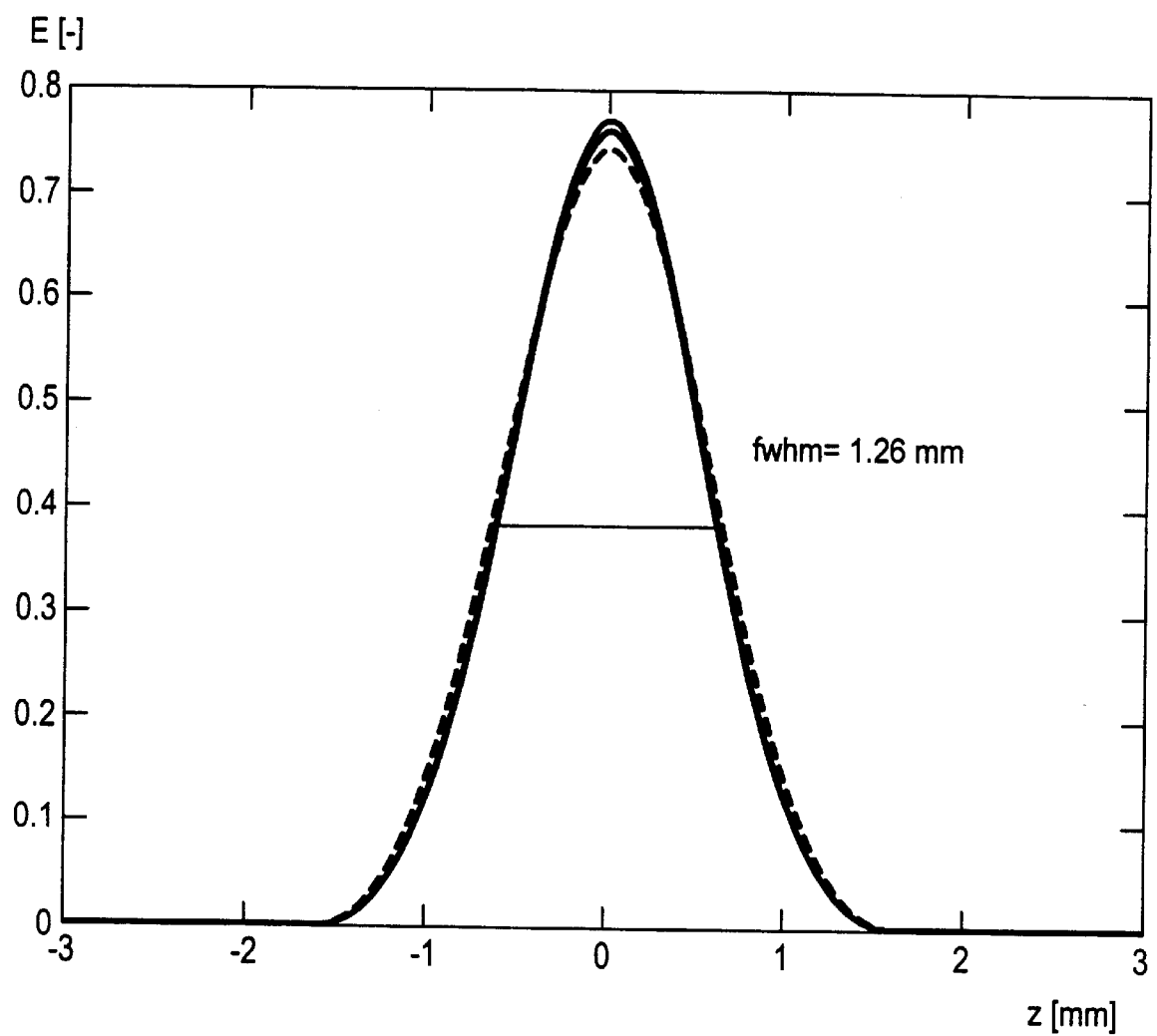
FIG. 4 shows the slice sensitivity profile in the spatial domain for three different time weighting functions that can be achieved with a CT apparatus having a 4-line detector that operates according to the inventive method.

FIG. 4 shows the slice sensitivity profile in the spatial domain, i.e. in the z-direction, for a spiral scan with a 4-line detector given a pitch p=1.5, with the measured signal caused by a subject having a defined attenuation value being entered as a dimensionless quantity E over the z-direction and z=0 corresponds to the position of the image plane in the z-direction. FIG. 4 shows the slice sensitivity profile for three different time weighting functions w( ). The weighting function g( ) in z-direction was retained unmodified for all three time weighting functions. The weighting function g( ) is a triangle whose width was selected such that the same slice sensitivity profile occurs as in the case of a 360LI interpolation for pitch 1 and a single-line detector. Practically the same slice sensitivity profile in the z-direction occurs in all three cases independently of the time resolution.

Figure 5:
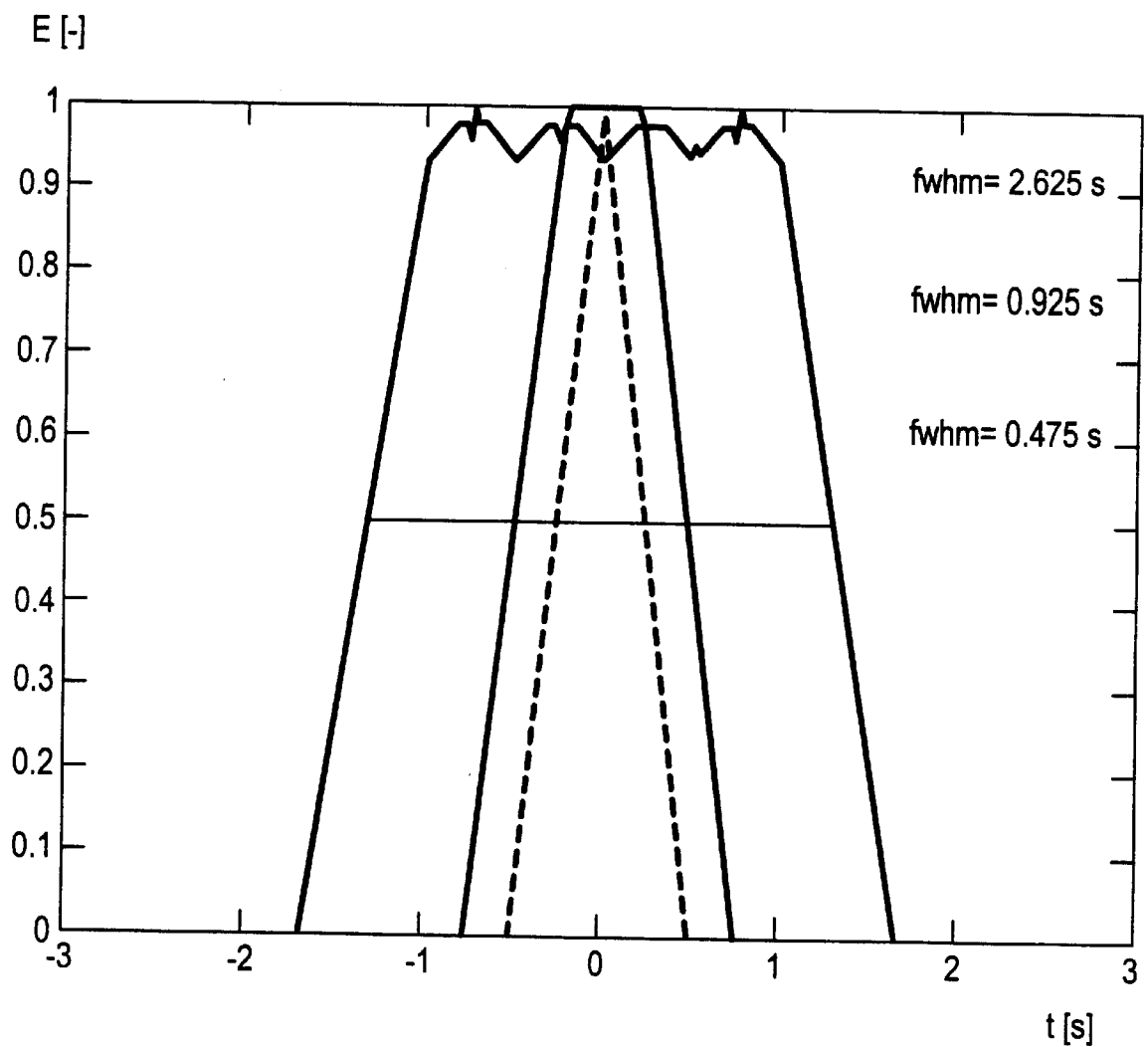
FIG. 5 shows the time sensitivity profile for three different time weightings that can be achieved with a CT apparatus having a 4-line detector that operates according to the inventive method.

FIG. 5 shows the corresponding time sensitivity profiles for a spiral scan which a 4-line detector given a pitch p=1.5 and a rotation time of 1 s, the dimensionless quantity E being entered over the time t. The maximum distance of the measured values weighted with the weighting function is selected such that, when the computer 8 does not implement a time weighting, i.e., it treats all projections the same insofar as their time position is concerned, a time window having the half-value width 2.65 s derives. FIG. 5 also shows the time sensitivity profiles for two time weighting functions that lead to time half-value widths of 0.925 s and 0.475 s (given 1 s rotation time). For the time half-value width 0.475 s, w( ) is a triangular function with the base width 1 s and, for the half-value width 0.925, w( ) is a triangular function with the base width 2 seconds.

FIGS. 6 through 9 demonstrate how the relationship of dose utilization and z-resolution can be arbitrarily set with a given time sensitivity profile and how the relationship of dose utilization and time resolution can be arbitrarily set with a given spatial slice sensitivity.

Figure 6:
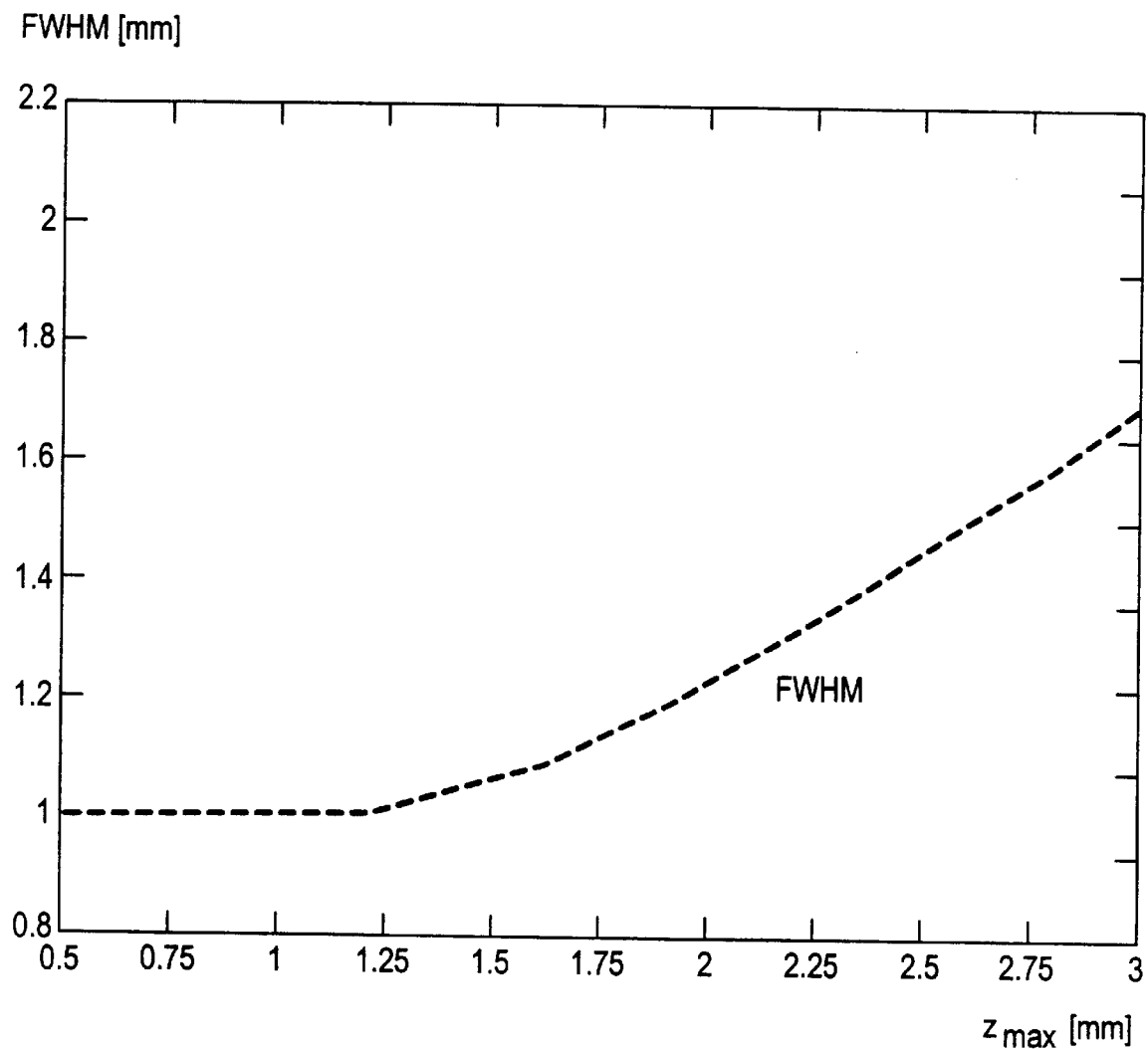
FIG. 6 shows the slice thickness as function of the width of the spatial weighting function for a CT apparatus having a 4-line detector that operates according to the inventive method.
Figure 7:
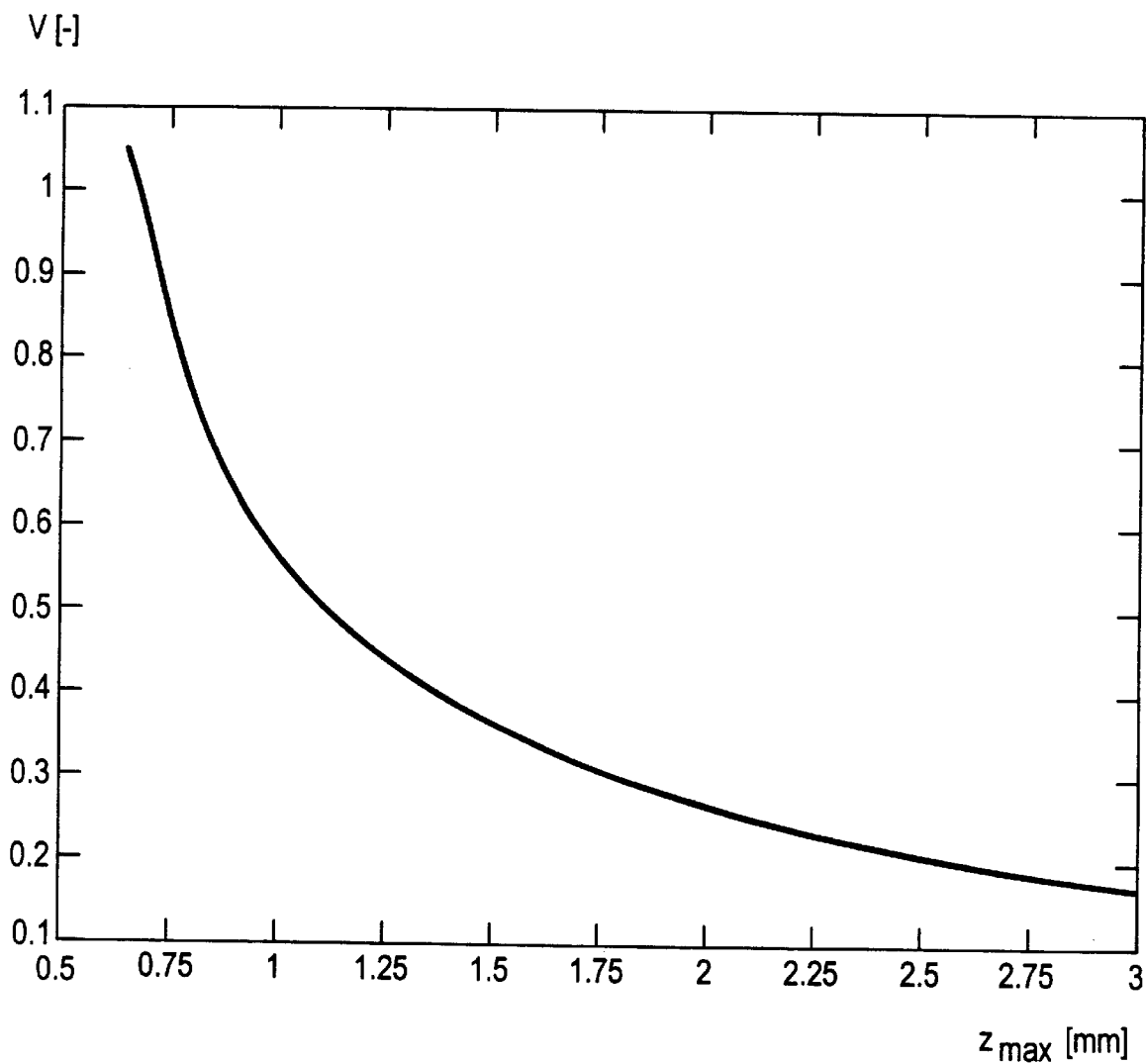
FIG. 7 shows the variance of the pixel noise given a constant mA value as a function of the width of the spatial weighting function for a CT apparatus having a 4-line detector that operates according to the inventive method.

A spiral scan with a 4-line detector given the pitch p=1.5 and a rotation time of 1 s was again utilized as an example. The weighting function w( )=constant was selected for FIGS. 6 and 7, i.e. all projections were treated the same independently of their measuring time. The time window contributing to the reconstruction therefore has the half-value width 2.65 s (see above). The weighting function g( ) in the z-direction is a triangle. FIG. 6 shows how the half-value width FWHM of the slice sensitivity profile in the z-direction increases with increasing base width $z_{max}$ of the function g( ). FIG. 7 shows how, given a fixed mA value of the X-ray source, the variance V of the pixel noise correspondingly decreases with increasing base width $z_{max}$ of the function g( ), i.e., the CT images have less noise at the expense of reduced z-resolution. At the same time, however, the sub-volume artifacts also decrease. The variance V=1 in FIG. 7 corresponds to the variance V of the pixel noise of a spiral scan implemented with a single-line detector with the same collimated slice thickness as in the case of FIG. 7.

Figure 8:
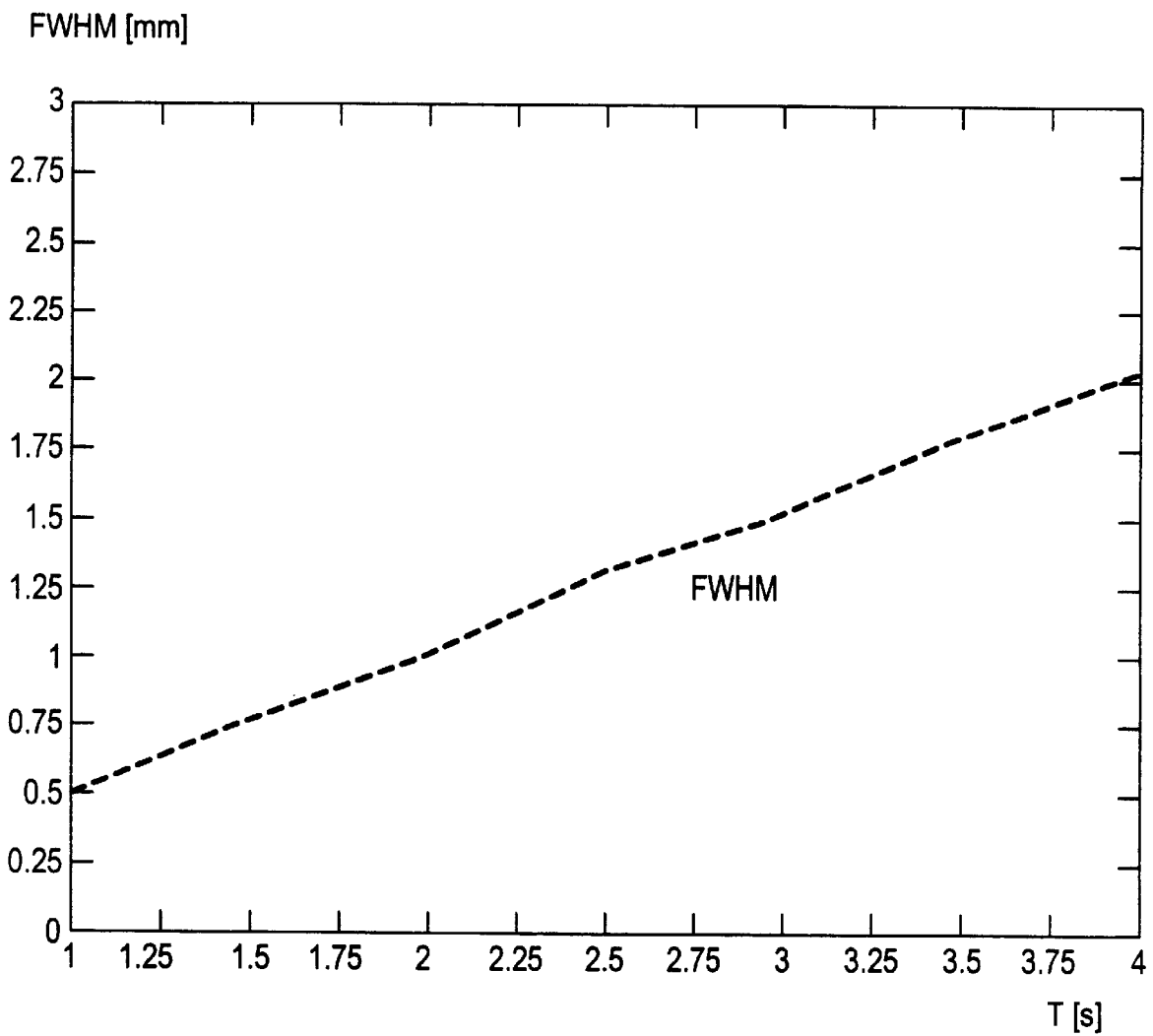
FIG. 8 shows the time slice thickness as function of the width of the time weighting function for a CT apparatus having a 4-line detector that operates according to the inventive method.
Figure 9:
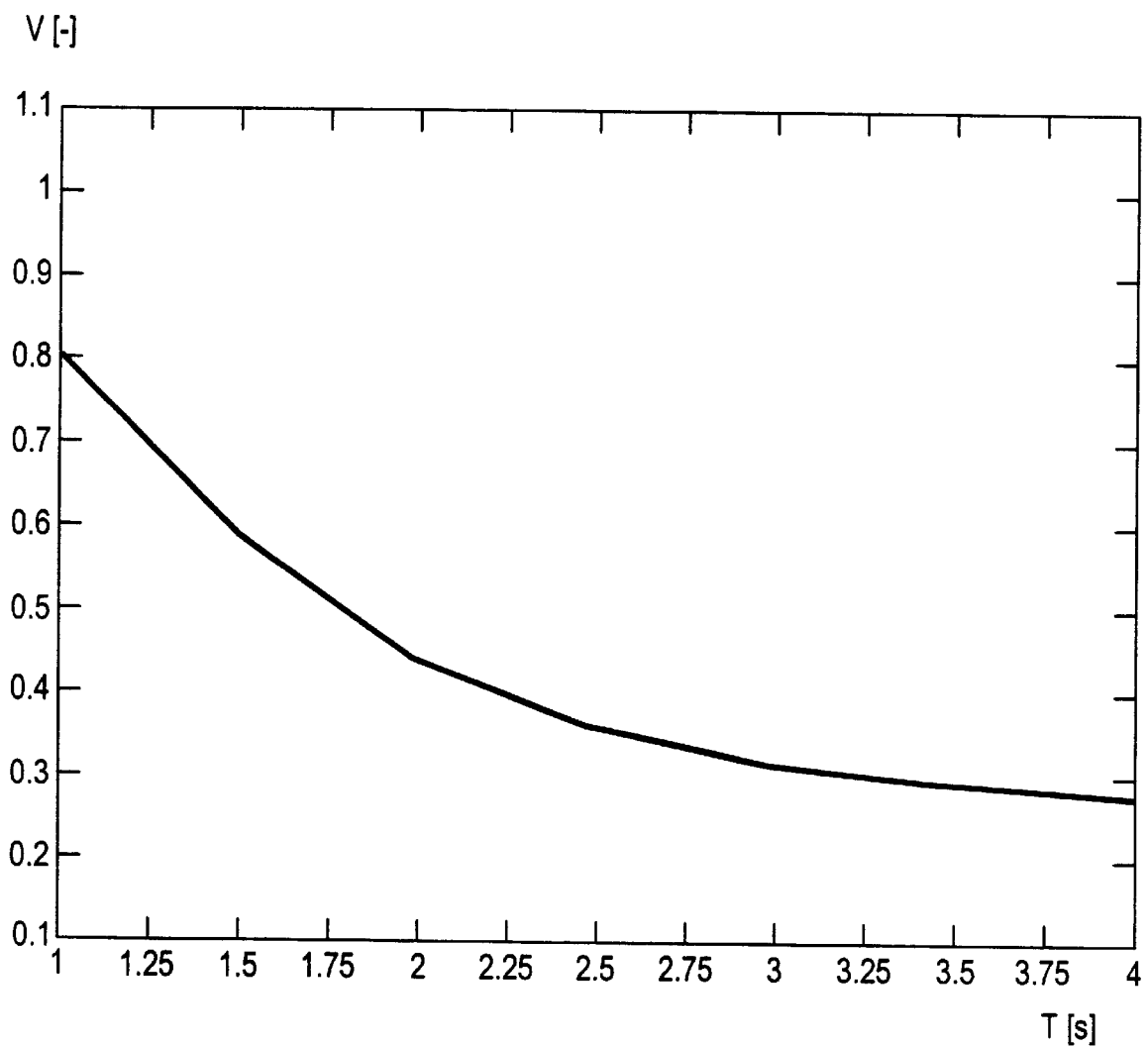
FIG. 9 shows the variance of the pixel noise given a fixed mA value as a function of the width of the time weighting function for a CT apparatus having a 4-line detector that operates according to the inventive method.

A fixed weighting function g( ) was selected for FIGS. 8 and 9, this being a triangle with a base width of two collimated slice thicknesses in all instances. Instead, the width $T_{max}$ of the triangular time weighting function w( ) was varied. FIG. 8 shows how the half-value width FWHM of the time sensitivity profile increases with increasing base width $T_{max}$ of the function w( ). FIG. 9 demonstrates how the variance of the pixel noise correspondingly decreases given a fixed mA value of the X-ray source. The obtainable lower limit for the variance is the value derived from FIG. 7 for the width of the weighting function g( ).

The first and the second weighting functions g( ) and w( ) can be triangular functions, as explained above, however, other forms such as, for example, rectangular, sinusoidal, etc., are also possible.

The forms of the first and of the second weighting functions g( ) and w( ) can be entered via the keyboard 12, as can their widths $z_{max}$ and $T_{max}$, i.e. the maximum distance from the image plane in the z-direction and the maximum time interval from the reference time. The position of the image plane in the z-direction as well as the position of the reference time, moreover, can also be set via the keyboard 12.

The described exemplary embodiment is a CT apparatus of the third generation. A CT apparatus of the fourth generation, which has a stationary, annular detector instead of an arcuate detector rotating together with the x-ray source, can be constructed and operated according to the inventive method.

The present invention can be utilized in medical and non-medical applications.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for reconstructing an image of a slice of an examination subject, said slice having a slice thickness with respect to an image plane, using a spiral scan computed tomography apparatus having an x-ray source which emits an x-ray beam and a radiation detector, comprising at least one line of detector elements, said x-ray beam rotating around an examination subject to conduct a spiral scan having a longitudinal axis associated therewith, with a relative shift along said longitudinal axis of the x-ray source and the detector occurring with respect to the examination subject during each revolution, said radiation detector producing measured values respectively allocated to one of a plurality of projection angles α and to a z-position on said longitudinal axis, while adhering to a constant, dimensionless pitch p during the spiral scan, said pitch being the ratio of said relative shift and a width along said longitudinal axis of a line of said radiation detector, said method comprising the steps of:

defining a reference time associated with said spiral scan;

for each projection angle, defining a set of measured values allocated to the projection angle which lie within a maximum distance from the image plane and which were obtained within a maximum time from said reference time;

weighting the measured values in said set, to produce a set of weighted measured values, using a first weighting function dependent on the respective spatial distances of the measured values along said longitudinal axis, and using a second weighting function dependent on the respective times of said measured values relative to said reference time; and reconstructing an image of said slice from said set of weighted measured values.

2. A method as claimed in claim 1 comprising employing a constant value as said second weighting function.

3. A method as claimed in claim 1 wherein the step of reconstructing an image of said slice comprises reconstructing an image of said slice using respective sets of weighted measured values for a plurality of projection angles each having a z-position allocated thereto which coincides with said image plane.

4. A method as claimed in claim 3 wherein said first weighting function and said second weighting function produce a plurality of respective weightings for said measured values, and wherein the step of reconstructing an image of said slice comprises adding all of said weightings for said weighted measured values in said set of weighted measured values to obtain a sum, and normalizing said set of weighted measured values with said sum.

5. A method as claimed in claim 4 wherein each projection angle has a calculated projection associated therewith, and wherein the respective calculated projections for said projection angles are parallel projections.

6. A method as claimed in claim 5 comprising acquiring said parallel projections by one-dimensional azimuthal interpolation from the respective sets of measured values for each projection angle.

7. A method as claimed in claim 6 wherein said radiation detector has a plurality of lines of detector elements and wherein each parallel projection is obtained with a respective line of detector elements without reference to said z-position of said lines of detector elements.

8. A method as claimed in claim 7 wherein each revolution is comprised of two half-revolutions, and said method comprising the additional steps of allocating respective half-revolutions to the respective parallel projections to distinguish between direct projections and complementary projections.

9. A computed tomography apparatus which produces an image of a slice of an examination subject, said slice having a slice thickness with respect to an image plane, comprising:

an x-ray source which emits an x-ray beam and a radiation detector, comprising at least one line of detector elements, for conducting a spiral scan, having a longitudinal axis, of an examination subject by rotating said x-ray beam around the examination subject with a relative shift of the x-ray source and the detector along said longitudinal axis occurring with respect to the examination subject during each revolution, said radiation detector producing measured values respectively allocated to one of a plurality of projection angles $\alpha$ and to a z-position on said longitudinal axis, while adhering to a constant, dimensionless pitch p during the spiral scan, said pitch being the ratio of said relative shift and a width along the longitudinal axis of a line of said radiation detector;

means for defining a reference time associated with said spiral scan and a maximum spatial distance relative to said image plane and a maximum time relative to said reference time; and computer means for, for each projection angle, defining a set of measured values allocated to the projection angle which lie within said maximum distance and which were obtained within said maximum time, and for weighting the measured values in said set, to produce a set of weighted measured values, using a first weighting function dependent on the respective spatial distances along said longitudinal axis of the measured values from the image plane, and using a second weighting function dependent on the respective times of said measured values relative to said reference time, and said computer means reconstructing an image of said slice from said set of weighted measured values.

10. A computed tomography apparatus as claimed in claim 9 further comprising means for setting at least one of said first weighting function and said second weighting function.

11. A computed tomography apparatus as claimed in claim 9 wherein said computer means comprises means for calculating, in advance of said spiral scan, first weightings associated with said first weighting function and second weightings associated with said second weighting function and for storing said first and second weightings in a table, and wherein the step of using said first weighting function comprises calling said first weightings from said table and wherein the step of using said second weighting function comprises calling said second weightings from said table.

12. A computed tomography apparatus as claimed in claim 9 wherein the step of rotating said x-ray source and said radiation detector around said examination subject comprises irradiating said examination subject during each revolution from a plurality of successive positions of a focus of said x-ray source along a helical path, with an x-ray beam from said focus striking said radiation detector at at least one line thereof to produce measured values for respective projections.

* * * * *